United States Patent
Yazaki et al.

(10) Patent No.: US 7,494,801 B2
(45) Date of Patent: Feb. 24, 2009

(54) **METHOD OF SELECTING *ESCHERICHIA COLI* STRAIN WHICH HIGHLY EXPRESSES EXOGENOUS GENES, *ESCHERICHIA COLI* MUTANT STRAINS SELECTED BY THIS METHOD AND PROCESS FOR PRODUCING ENZYMES AND COMPOUNDS USING THE SAME**

(75) Inventors: Kazufumi Yazaki, Kyoto (JP); Hirobumi Aoki, Chiba (JP); Harumi Kamachi, Chiba (JP)

(73) Assignee: Showa Denko K.K., Tokyo (JP)

( * ) Notice: Subject to any disclaimer, the term of this patent is extended or adjusted under 35 U.S.C. 154(b) by 14 days.

(21) Appl. No.: 10/538,291

(22) PCT Filed: Dec. 11, 2003

(86) PCT No.: PCT/JP03/15882

§ 371 (c)(1),
(2), (4) Date: Jun. 10, 2005

(87) PCT Pub. No.: WO2004/053111

PCT Pub. Date: Jun. 24, 2004

(65) Prior Publication Data

US 2006/0234331 A1    Oct. 19, 2006

(30) Foreign Application Priority Data

Dec. 12, 2002   (JP) ............................ 2002-360564

(51) Int. Cl.
| | |
|---|---|
| *C12N 1/20* | (2006.01) |
| *C12N 9/00* | (2006.01) |
| *C12P 13/04* | (2006.01) |
| *C07H 21/04* | (2006.01) |

(52) U.S. Cl. .................. 435/252.33; 435/34; 435/106; 435/183; 435/69.1; 536/23.2

(58) Field of Classification Search .................. None
See application file for complete search history.

(56) References Cited

FOREIGN PATENT DOCUMENTS

| | | |
|---|---|---|
| EP | 866132 A2 | 3/1998 |
| EP | 1 132 464 A2 | 9/2001 |
| JP | 8-140671 | 6/1996 |
| JP | 10-313863 | 12/1998 |
| JP | 2003-225092 | 8/2003 |
| WO | WO 94/19472 | 9/1994 |
| WO | WO 01/66776 A2 | 9/2001 |
| WO | WO 03/000915 A1 | 1/2003 |

OTHER PUBLICATIONS

Rowbury et al. ( J. appld Microbiol 2001, 90, 677-695).*
Seaver et al. ( J. Bacterol. 2001. pp. 7182-7189).*
Rowe et al. ( Appld and Env. Microbiol 1998, 65, 2710-2715).*
Yazaki K. et al., "cDNA Cloning and Gene Expression of Phenylalanine ammonia-lyase in Lithospermum Erythrorhizon" Biosci. Biotechnol. Biochem. vol. 61, No. 12, (1997), pp. 1995-2003.
Baedeker M et al., "Overexpression of a designed 2.2 kb Gene of Eukaryotic Phenylalanine Ammona-lyase in *Escherichia coli*", FEBS Lett., vol. 457 No. 1, (1999), pp. 57-60.
Kamachi et al., "Shokubutsu Koso Fusei Han' noho Ni Yoru Hiten' nenkei Amino-san Gosei" Bio Industry, Mar. 12, 2003, vol. 20, No. 3, pp. 12-20.

* cited by examiner

*Primary Examiner*—Rebecca E Prouty
*Assistant Examiner*—MD. Younus Meah
(74) *Attorney, Agent, or Firm*—Sughrue Mion, PLLC (57) ABSTRACT

The invention relates to a selection method of an *Escherichia coli* mutant strain which expresses an exogenous gene at a high level, wherein stress resistance such as hydrogen peroxide decomposition activity is used as an index, the *Escherichia coli* mutant strain selected thereby and production methods of enzyme using the strain and of useful compounds like amino acids (especially L-amino acid) and the like using the strain. According to the selection method of the invention, an *Escherichia coli* mutant strain where gene expression amount does not decrease with passage can be obtained, and a compound using a plant-derived ammonia lyase can be efficiently produced.

1 Claim, 2 Drawing Sheets

CBB-stain  Western-Blot a; MW maker
b; *E. coli* XL1Blue (host cell)
c; No. 16 (Example 6, High activity strain)
d; No. 24 (Example 7, Low activity strain)
e; No. 12 (Example 7)
10%-20% gradient gel, 40mA, 60min

```
SEQUENCE LISTING

<160> NUMBER OF SEQ ID NOS: 2

<210> SEQ ID NO 1
<211> LENGTH: 18
<212> TYPE: DNA
<213> ORGANISM: Lithospermum erythrorhizon

<400> SEQUENCE: 1
taagcgtaat tagctgag                                                 18

<210> SEQ ID NO 2
<211> LENGTH: 18
<212> TYPE: DNA
<213> ORGANISM: Lithospermum erythrorhizon
```

-continued

```
<400> SEQUENCE: 2
agatcgaaga tctaaaca                                                    18
```

METHOD OF SELECTING *ESCHERICHIA COLI* STRAIN WHICH HIGHLY EXPRESSES EXOGENOUS GENES, *ESCHERICHIA COLI* MUTANT STRAINS SELECTED BY THIS METHOD AND PROCESS FOR PRODUCING ENZYMES AND COMPOUNDS USING THE SAME

TECHNICAL FIELD

The present invention relates to a method for selecting *Escherichia coli* strain which highly expresses an exogenous gene, *Escherichia coli* selected by this selecting method, and a process for producing an enzyme and a compound using this strain. More specifically, it relates to a method for selecting from a transformant group having introduced therein an enzyme gene whose expression is unstable in *Escherichia coli*, a mutant strain in which the gene is highly expressed stably, a mutant strain selected thereby which highly expresses an exogenous gene, and a process for producing an enzyme and a compound, especially an ammonia lyase and an amino acid using this strain.

BACKGROUND ART

The expression of exogenous genes using *Escherichia coli* is a field on which a great many studies and developments of practical techniques have been made, and the field is one of the most advanced fields in molecular biology and genetic engineering. Nowadays, it has quite a high significance as a production process in industries, and a large number of biomedics have been industrially produced by a process using *Escherichia coli*.

*Escherichia coli* strain which has been used most frequently in studies of molecular biology is a strain derived from K12 strain (Swartz, 1996, In *Escherichia coli* and Salmonella, Cellular and Molecular Biology, 2nd edition, ASM Press Washington, p.p. 1693-1711). In recent years, a strain derived from *Escherichia coli* B strain such as BL21 has been often used, and a list of strains which have been most frequently used for production of recombinant proteins has been presented by Wingfield, 1997 (Current Protocols in Protein Science, Coligan et al., Ed. John Wiley & Sons, Inc. 5.0.1-5.0.3).

A large number of systems in which proteins are expressed in bacterial hosts have been described in a document (Makrides, 1996, Microbiol. Rev. 60: 512-538; Current Opinions in Biotechnology, 1996, 7). An expression system comprises a promoter, its regulator, a ribosome immobilization site, a restriction site in whose downstream a useful gene can be introduced, a structure which can serve as a transcription terminator, a gene which is arbitrarily present in order to improve qualities of a super-expressed useful protein by simultaneous expression, and one or more vectors capable of introducing a combination of these into a host.

These vectors exist in cells in a predetermined copy number which is determined by interaction of two RNAs encoded by plasmids RNA I and RNA II (Polisky, 1988, Cell 55: 929-932). Regarding control of the copy number of expression plasmids in *Escherichia coli*, plural strategies have been described in documents (Swartz, 1996, In *Escherichia coli* and Salmonella, Cellular and Molecular Biology, 2nd edition, ASM Press Washington, p.p. 1693-1711, Makrides, 1996, Microbiol. Rev. 60: 512-538; Current Opinions in Biotechnology, 1996, 7).

When an exogenous gene is expressed by being incorporated into *Escherichia coli*, "compatibility" is required among an exogenous gene to be expressed, *Escherichia coli* and its gene expression system, and they are generally selected by a try-and-error method. Examples of cases where a desired protein is not obtained in a sufficient amount include a case in which a protein produced cannot obtain a normal structure inherent in the protein and becomes a precipitate (inclusion body) and a case in which a protein is decomposed immediately after produced. Many methods for solving such problems have been also introduced in documents (JP-A-10-313863, JP-A-8-140671, Makrides, 1996, Microbiol. Rev. 60, 512-538, Current Opinions in Biotechnology, 1996, 7).

As stated above, even with a lot of information and a huge number of expression systems and *Escherichia coli* strains, there are still a large number of genes which are hardly expressed stably, and in a great many cases where attempts to obtain proteins by expressing desired exogenous genes are made, proteins cannot be obtained in satisfactory quantities. Further, it is a phenomenon frequently observed that even purpose designed *Escherichia coli* strains are decreased in gene expression during storage or subculture, and what causes such a phenomenon is still unknown in many cases. For example, the present inventors invented a process for producing L-amino acids from various cinnamic acids using an amino group addition reaction of an enzyme ammonia lyase, and filed a patent application directed to the invention (JP-A-2003-225092). During the research process for the invention, a phenomenon that when *Escherichia coli* was transformed to express an enzyme ammonia lyase, activity of the transformant was decreased with each passage. This decrease in activity with passage is not attributed to methylation of an expression control site, plasmid loss, plasmid mutation and the like as generally mentioned as causes for decreased activity, and it cannot be avoided by any known information.

In case of basic studies in which the purpose can be attained by small-scale culture, problems are generally solved by conducting transformation again to obtain a new transformant. However, in case of relatively large-scale industrial production which involves multiple passages to take a long culture time, unstable gene expression is quite a serious problem.

However, among problems on stabilization of gene expression, those ever taken up and studied are only problems regarding prevention of loss of an exogenous gene due to loss of a plasmid and avoidance of deficient transcription due to modification or mutation of a plasmid. No measure against decrease in expression due to mutation of a host itself has ever been discussed. This is presumably because most of *Escherichia coli* strains used in laboratories as hosts are mutant strains modified to be held stably without mutation or modification of plasmids and there seems no information on further modification thereof. Moreover, the problems can be avoided by modification of exogenous genes including plasmids in some cases. Ordinarily, rather than mutation of host *Escherichia coli* strains, modification of exogenous genes as a proven method which has so far made some technical achievements has been attempted in many cases. However, modification of exogenous genes is a work which is time-consuming and laborious, and it is not always successful. In addition, there has been no approach to cope with expression of genes which cannot be stabilized even by modification of exogenous genes.

DISCLOSURE OF THE INVENTION

The objects of the invention are to provide an *Escherichia coli* mutant strain useful in obtaining a sufficient amount of protein from an exogenous gene unstably expressed whose expression amount tends to decrease during subculture or storage and to provide a process for producing an industrially important chemical substance using the strain.

More specifically, the invention provides an *Escherichia coli* mutant strain in which expression of an exogenous gene apt to decrease due to causes other than loss, mutation and modification of a plasmid is stabilized and a process for producing an industrially important chemical substance using the strain.

Especially, the invention provides an *Escherichia coli* mutant strain in which expression of a plant-derived phenylalanine ammonia lyase gene having a strong tendency to decrease in *Escherichia coli* without being accompanied by a defective plasmid is stabilized and a process for producing industrially important amino acids using the strain.

The present inventors have assiduously conducted investigations to achieve the foregoing objects, and have consequently found that by selecting an *Escherichia coli* strain using as an index hydrogen peroxide decomposition activity which is a stress resistance property having no direct relation with protein production, a mutant strain in which gene expression amount does not decrease during subculture can be obtained, and completed the invention based on this finding.

That is, the invention is to provide an *Escherichia coli* mutant strain useful in obtaining a sufficient amount of protein from an exogenous gene which tends to be unstably expressed and decrease in expression amount during subculture or storage, and a process for producing an industrially important chemical substance using the strain.

That is, the invention provides, as stated below, a method for selecting an *Escherichia coli* strain, *Escherichia coli* strain selected thereby, a process for producing an enzyme using the same, and a process for producing a useful compound using the enzyme.

[1] A method for selecting an *Escherichia coli* strain which highly expresses an exogenous gene, comprising selection using the intensity of stress response as an index.

[2] The selection method according to 1, wherein the stress response is hydrogen peroxide decomposition activity.

[3] The selection method according to 1 or 2, wherein the strain to be selected is one where an exogenous gene whose expression tends to decrease by causes other than loss or mutation of a plasmid when introduced into an *Escherichia coli* is highly expressed.

[4] An *Escherichia coli* strain which highly expresses an exogenous gene, the strain being selected using the intensity of stress response as an index.

[5] The *Escherichia coli* strain which highly expresses an exogenous gene according to 4, wherein the stress response is hydrogen peroxide decomposition activity.

[6] The *Escherichia coli* strain which highly expresses an exogenous gene according to 4 or 5, wherein an exogenous gene whose expression tends to decrease by causes other than loss or mutation of a plasmid when introduced into an *Escherichia coli* is highly expressed.

[7] The *Escherichia coli* strain which highly expresses an exogenous gene according to any one of 4 to 6, wherein the initial amount of gene expression is maintained or enhanced during subculture when a gene, whose expression amount in other *Escherichia coli* strains is reduced to half the initial expression amount during 30 subculture generations, is expressed in the strain.

[8] The *Escherichia coli* strain which highly expresses an exogenous gene according to 6 or 7, wherein the exogenous gene whose expression decreases by causes other than loss or mutation of a plasmid is a gene of an ammonia lyase.

[9] The *Escherichia coli* strain which highly expresses an exogenous gene according to 8, wherein the expression gene of an ammonia lyase is a gene of phenylalanine ammonia lyase.

[10] The *Escherichia coli* strain which highly expresses an exogenous gene according to 9, wherein the gene of phenylalanine ammonia lyase is derived from a plant.

[11] The *Escherichia coli* strain which highly expresses an exogenous gene according to 10, wherein the plant is *Lithospermum erythrorhizon*.

[12] The *Escherichia coli* strain which highly expresses an exogenous gene according to any of 4 to 11, wherein the *Escherichia coli* strain is derived from K12 strain.

[13] The *Escherichia coli* strain which highly expresses an exogenous gene according to 12, wherein the *Escherichia coli* strain is derived from XL1-Blue strain.

[14] The *Escherichia coli* strain which highly expresses an exogenous gene according to 13, wherein the *Escherichia coli* strain is *Escherichia coli* SD840 strain.

[15] The *Escherichia coli* strain which highly expresses an exogenous gene according to 14, wherein the *Escherichia coli* strain is a derivative strain obtained from *Escherichia coli* SD840 strain by clone selection or gene manipulation.

[16] *Escherichia coli* SD840 strain (Deposit No. FERM BP-08546).

[17] A process for producing an enzyme, comprising expressing the exogenous gene of the *Escherichia coli* strain which highly expresses the exogenous gene according to any one of 4 to 15.

[18] A process for producing a compound, comprising reacting a treating solution containing the *Escherichia coli* strain which highly expresses the exogenous gene according to any one of 4 to 15 or an enzyme thereby produced with a substrate of the enzyme.

[19] The process for producing a compound according to 18, wherein the enzyme is an ammonia lyase, the substrate is an unsaturated carboxylic acid, and the resulting compound is an L-amino acid and/or its derivatives.

MODE FOR CARRYING OUT THE INVENTION (1) Method for Selecting an *Escherichia coli* Strain which Allows High Expression In the invention, an *Escherichia coli* strain which highly expresses an exogenous gene stably refers to a strain whose expression amount is relatively large when an exogenous gene is introduced into *Escherichia coli* by an ordinary method and whose expression is stable. An exogenous gene to be expressed is not particularly limited, and the invention is especially useful when introducing "an exogenous gene hard to express". Here, "an exogenous gene hard to express" refers to an exogenous gene whose expression amount decreases during subculture when it is introduced into *Escherichia coli* for transformation and the transformant *Escherichia coli* is subcultured. More specifically, it refers to an exogenous gene whose expression amount decreases due to causes other than loss or mutation of a plasmid. Further, it refers to an exogenous gene which does not conduct protein production notwithstanding that there is no defect such as loss or mutation of a plasmid, even when introduced into *Escherichia coli* by being incorporated into an expression plasmid of *Escherichia coli* in a manner that the gene can readily be expressed.

The method for selecting an *Escherichia coli* mutant strain in the invention is described in detail below. By the way, induction of mutation or the like can be carried out, unless otherwise instructed, by referring to a method described in, for example, Sambrook, J. et al., Molecular Cloning: A Laboratory Manual, 2nd ed., Cold Spring Harbor Laboratory Press, New York, 1989.

First, a process for producing an *Escherichia coli* mutant strain is described. Selection of the mutant strain is conducted using a transformant obtained by transforming host *Escherichia coli* with a recombinant vector having a gene hard to express. In preparation of a recombinant vector, an expression plasmid having a sequence necessary for control of expression in *Escherichia coli*, for example, commercially available one such as pET, pTrc99A, pKK233 or pUC18 can be used. A recombinant vector having a gene hard to express introduced in an appropriate site of such an expression plasmid is constructed, i.e., an *Escherichia coli* recombinant vector comprising a hard-to-express gene present in series with a ribosome binding site, a structure capable of functioning as a transcription terminator, a marker gene and the like in the downstream of an *Escherichia coli* promoter and its regulator, preferably, a hybrid promoter such as lac promoter, Trp promoter or Tac promoter, T5 promoter or T7 promoter is constructed.

The *Escherichia coli* strain to be transformed in the invention is not particularly limited. K12 strain, B strain and the like are preferably used. In view of biological containment, K12 strain is advantageously used. Strains which are widely used as an *Escherichia coli* host with stable form and properties can be used, and examples thereof include commercially available products such as XL1-Blue strain (Stratagene; which can be procured from TOYOBO in Japan (Bullock, Fernandez & Short, 1987, Biotechniques, 5:376-378), JM109 strain (which can be procured from TAKARA SHUZO CO., LTD.) and HB101 strain.

A transformant is spread on an agar plate medium, preferably an M9 glucose plate, obtained by adding to an ordinary medium capable of growing *Escherichia coli*, an appropriate amount of a transformant selection substance (for example, antibiotics such as ampicillin) in accordance with a recombinant vector to be used, and further adding agar for plating. Culture is conducted from 20° C. to 40° C., preferably from 25° C. to 35° C., more preferably from 25° C. for 16 to 72 hours until colonies are clearly formed, preferably from 24 to 48 hours.

A transformant having a gene hard to express forms non-uniform colonies in many cases. In the invention, selection is conducted from among the transformant strains using intensity of stress response as an index. The type of stress response which can be used is not particularly limited. Examples thereof include hydrogen peroxide decomposition activity and growth recovery after heat treatment (heat resistance). Of these, hydrogen peroxide decomposition activity is preferable because when colonies are reacted with a trace amount of a hydrogen peroxide solution, intensity of stress response can visually be estimated according to an amount of oxygen generated by decomposing hydrogen peroxide.

Selection may further be repeated, as required, using the same index as in the first selection. In the selection, among strains showing stress response, it is preferable that strains with its colony color close to white as compared to other strains and strains with its colony diameter significantly small be selected. With respect to the second selection of strains and thereafter, selection may be conducted by combinationally using analysis of the resulting proteins by a known method.

A recombinant vector used in selection can be dropped by subculturing the resulting mutant strain on a medium without chemical stress to thereby obtain a host *Escherichia coli* mutant strain.

Subculture stability of the obtained host *Escherichia coli* mutant strain can be evaluated by observing expression of an exogenous gene after subculturing the strain under ordinary growth conditions for a strain without causing selective pressures by chemicals until divisions are repeated a predetermined number of times. For example, if a test strain is inoculated on a nutrient medium such as LB broth in such an amount that initial turbidity becomes 0.1, and cultured until turbidity becomes 3 or more, the passage number will be of approximately 5 generations. Strains with 30-generation passage can be obtained by repeating the culture 6 times under the same conditions. The expression of an exogenous gene of the strain can be evaluated, for example, by using a production amount of protein derived from the exogenous gene as an index.

During the selection of the mutant strain, it is not necessary in particular to conduct mutation treatment. However, according to the type of host *Escherichia coli* used, it is sometimes advantageous to subject the host *Escherichia coli* to ordinary mutation treatment such as ultraviolet irradiation or mutation agent treatment.

The thus-obtained *Escherichia coli* mutant strain of the invention is not different from its parent strain in growth rate, transformation method, storage method and the like, and it can be treated in a usual nutrient medium by a usual procedure in a temperature range of 25° C. to 37° C.

The reason why a strain having high stress response has high expression and high activity is not clear. It is however presumably related to the fact that expression of an exogenous gene is a type of stress. Besides, since high stress response can be considered to act to suppress expression of an exogenous gene and alleviate stress, the finding that a strain having high stress response has high expression and high activity according to the invention could not have been expected at all.

(2) *Escherichia coli* Strain which Allows Stable High Expression

The invention provides an *Escherichia coli* strain selected by the foregoing method. The *Escherichia coli* strain selected by the invention is, as noted above, an *Escherichia coli* strain which highly expresses an exogenous gene stably in an arbitrary transformant strain of a substantially arbitrary *Escherichia coli* strain.

Examples of the thus-obtained mutant strain include *Escherichia coli* SD840 strain. This is an *Escherichia coli* strain which allows high expression stably and which is selected by the foregoing method from a transformant obtained by using XL1-Blue strain as a parent strain and introducing a plant phenylalanine ammonia lyase gene therein. This strain produces an exogenous gene-derived protein in an amount 10 or more times larger than the amount of the protein produced by a parent XL1-Blue strain, and allows stable expression without change by passage of 30 generations of the transformant.

*Escherichia coli* SD840 strain was deposited in International Patent Organization Depositary, National Institute of Advanced Industrial Science and Technology, AIST Tsukuba Central 6, 1-1-1 Higashi, Tsukuba, Ibaraki, Japan (postal cord305-8566) (deposit date: Sep. 27, 2002, Deposit No. FERM P-19047), and transferred to International Depositary on Nov. 10, 2003 (International Deposit No. FERM BP-08546).

Outstanding characteristics of SD840 strain, one of *Escherichia coli* mutant strains obtained by the selection method of the invention, are listed below in comparison to those of the parent strain.

TABLE 1

| Characteristics | XL1-Blue | SD840 strain |
|---|---|---|
| Dyeing | + (pale yellow) | - (white) |
| Colony gloss | rough | glossy |
| Glycerol assimilation | + | - |
| Succinic acid assimilation | + | - |
| Hydrogen peroxide decomposition activity in logarithmic growth phase | low | high |

The properties of the *Escherichia coli* mutant strains of the invention are also shown as a result of genomic analysis of a latter growth phase (after a stationary phase), by characteristic genes which allow high expression in comparison to the parent strain. The genes include those whose function is not yet identified. They include those which are causes of stable expression of hard-to-express genes and those which are results of stable expression of hard-to-express genes, which shows characteristics of SD840 strain as one of the mutant strains in the invention. Characteristic genes which exhibits significantly high expression include oppA, ompA, tufB, tufA, fusA, gapA, rpsA, ahpC, infc, katE, ydiH, lacI, icdA, oppC, rpoB, ynhA, ompX, dnaJ, oppB, yceD, dnaK, aco2, cld, zipA, minC, galF, gnd, yafK, fabB, trmD, cysK, cydA, hslV, pepN, oppF, rpoC, ompF, rpoA, pheS, rpsB, oppD, pepD, serS, topA, grpE, yeaF, asnB, serC, ppiB, tolB, ycbK, ybeY, prsA, rpsG, gyrA, ahpF, tyrS, pheA, clpB, rpsL, cydB, asps, ybdR, ftsZ, aroG, rplJ, tsf, rpsP, Cnt5, rplA, aceA, mdh, ybgF, add, yjjZ, rplC, (erfK), dcp, glf, amn, aceB, rpsD, mopB, gpt, yaiL, rpoD, ynfB, pgmU, rplE, rfbB, seqA, asnS, zwf, eda, fabZ, otsA, Cnt5, lrp, ychB, pal, rplY, folE, rplN, glnS, rimM, yefG, ydcF, rlpA, yacA, fabD, Cnt5, rfbD, dicA, metG, ppc, (yeeT), yafJ, aspC, pyrC, leuS, ycbL, rplT, ykfF, sodB, 430#6, rnb, rpsE, yebC, rpsJ, 664#11, yliJ, ycfC, pnp, rfbA, ybiC, rplS, trpA, hupB, hisC, rplB, rpsH, pheT, yefI, lpdA, serA, lolA, wbbJ, leuC, rlpB, rplD, sucB, fkpB/slpA, ygfB, rplX, htpG, mopA, pntA, rpsF, infB, ycil, (yhhX), moaB, ycjX, glyQ, yagU, tolC, gcvR, gdhA, yadF, purB, speE, (yefJ), yggB, accA, ybiT, moaE, rpsK, yleA, mukE/kicA, prfB, ybaD, ibF, hslU, adk, rpsM, rplQ, nfnB, yfhF, yfiB, yaeS/uppS/rth, aroA, dapD, 221#15, tktA, (cybB), yhbH, hisH, pbpB/ftsI, ansA, gltB, bcp, gm4D, yoaB, 232#7, ugd, map, rfaL, rplW, rfbC, rplK, rpsC, glyS, speG, guaA, rpmB, rplF, ptsN, smtA, rpmA, ykgA, ompT, rplU, lspA, exoX, hisI, dacA, fabF, ycbW, sucD, 120#5, kdgK, trmU, lon, ntpA, yciM, tolQ, rfaP, rfaI, up18, yfgM, rplR, guaB, ribH, atpB, yaeL, atoE, yagB, pdxH, cspJ, rplM, rplO, potD, rfbX, yrfH/hslR, fcl/wcaG, trxB, plsX, gltX, dnaA, ydfG, priB, rpsN, yhcN, manA, surA, purE, secY/prlA, dxr, yeaJ, yfcB, dld, cysP, fbp, 323#1, intD, hupA, ftsL, aceK and codA.

(3) Process for Producing an Enzyme (Protein) with an *Escherichia coli* Strain Which Allows Stable High Expression The invention further provides a process for producing an exogenous protein, typically, an enzyme using the *Escherichia coli* mutant strain.

In the method for producing an enzyme and other proteins according to the invention, the *Escherichia coli* mutant strain is cultured, and expression is induced when necessary. As a method for culturing a transformant, a conventional method is used, and a medium may be either a nutrient medium or a synthetic medium. A culture purification is performed by an ordinary method used for purification of proteins, such as gel filtration or various kinds of column chromatography (for example, see "Current Protocols in Protein Science" (ed. Coligan, J. E. et al.), John Wiley and Sons, Inc., Chapter 6).

When the target protein is present in periplasm, purification can be conducted by referring to the Willsky et al. method (J. Bacteriol., 127, 595-609 (1976)).

The production method according to the invention can be applied to any enzymes and other exogenous proteins that can be produced by a gene introduced into *Escherichia coli*, and it is especially useful as a method for producing enzymes and other exogenous proteins which are produced by expression of genes whose expression in *Escherichia coli* has been so far difficult.

As the enzymes and other exogenous proteins, for example, a plant phenylalanine ammonia lyase and the like are mentioned. Especially, a plant phenylalanine ammonia lyase, for example, is quite a desirable example, because it is produced as an exogenous gene-derived protein in SD840 strain in an amount of 10 or more times the amount of the protein produced with the parent strain XL1-Blue strain and in stability without changing by subculture of the transformant through 30 generations.

The amount of the enzyme and other proteins produced by expression of the gene can be determined by ordinary SDS-PAGE, a western blotting method using an antibody or the like. When the protein is an enzyme, the quantitative determination may be conducted by measurement of activity or the like.

(4) Process for Producing an Amino Acid or the Like

The invention further provides a process for producing a useful substance using the *Escherichia coli* mutant strain. The *Escherichia coli* mutant strain is cultured by the foregoing method, and expression is induced as required. Significantly efficient an enzyme, the quantitative determination may be conducted by measurement of activity or the like.

(4) Process for Producing an Amino Acid or the Like

The invention further provides a process for producing a useful substance using the *Escherichia coli* mutant strain. The *Escherichia coli* mutant strain is cultured by the foregoing method, and expression is induced as required. Significantly efficient production of a substance can be conducted in comparison to the use of a wild strain by reacting the *Escherichia coli* mutant strain obtained from the culture solution or its treated product with a substrate that gives a desired substance to obtain the substance.

The useful substance produced by the invention varies with the type of the enzyme that the *Escherichia coli* mutant strain produces. For example, when the enzyme is a catabolic enzyme, a decomposed product of a substrate is obtained. When the enzyme is a transferase, a compound in which a predetermined group is added to a substrate or a compound in which a predetermined group is removed from a substrate is obtained. For example, with an ammonia lyase, an amino acid is formed by adding ammonia to an unsaturated bond of an unsaturated carboxylic acid in the presence of ammonia.

According to the invention, a reaction with cinnamic acids is conducted in the presence of ammonia using SD840 strain that highly expresses a plant phenylalanine ammonia lyase, whereby various corresponding optically active amino acids can be produced. SD840 strain is free from a problem such as a decrease in expression with passage or the like, making it possible to realize stable high production in scale-up production requiring multiple passages, which was impossible with the parent strain.

BEST MODE FOR CARRYING OUT THE INVENTION

The invention is described in more detail below by referring to Examples. However, the invention is not limited at all by these Examples. The conditions and the procedures in the following Examples are based on the method described in Sambrook, J. et al, "Molecular Cloning: A Laboratory Manual, 2nd ed.", Cold Spring Harbor Laboratory Press, New York, 1989.

In measurement of enzymatic activity in Examples, an amount of an enzyme that liberates cinnamic acid in an amount of 1 µmole/min at 30° C. in the presence of a 0.1 M sodium borate buffer solution pH 8.5 and 10 mM L-phenylalanine as a substrate was defined as 1 unit (U).

An amount of an enzyme protein was determined by a biuret method using bovine serum albumin as a standard.

With respect to cinnamic acid and L-phenylalanine, the reaction solution was separated and determined by HPLC under the following conditions.

Column: Shodex (registered trademark) RSpak NN-614 (manufactured by Showa Denko K.K.)

Column temperature: 40° C.

Eluent: acetonitrile/water/50 mM $H_3PO_4$—$KH_2PO_4$ aqueous solution (pH 3)=20/70/10

Flow rate: 1.0 ml/min

Detection: by UV absorption at 210 nm

In culturing a transformant, M9 medium (0.6% disodium hydrogenphosphate, 0.3% potassium dihydrogenphosphate, 0.05% sodium chloride, 0.1% ammonium chloride, 0.1% glucose, 1 mM magnesium sulfate, 0.001% thiamine hydrochloride and 0.1 mM calcium chloride, pH 7.4) containing 100 ppm ampicillin or an LB medium (1% polypeptone, 0.5% yeast extract and 1% sodium chloride) containing 100 ppm ampicillin was used. According to the use, an agar plate medium solidified by adding 2% agar to each medium was employed.

The enzymatic activity of the transformant was measured as follows. Cells were collected by centrifugation from a culture solution obtained by culture in 5 to 100 ml of the above-described medium at 25° C. for 38 hours or more. The resulting cells were washed with a physiological saline solution in the same volume as that of the culture solution, and then suspended in a reaction solution (4M ammonia/ammonium carbonate (pH 10.3)) of a volume half the volume of the culture solution. A substrate at a final concentration of 0.2% (2,000 mg/L) was added thereto, and the reaction was conducted at 30° C. with shaking. A part of the reaction solution was taken in an appropriate time (usually between 2 and 6 hours), and cells were removed by centrifugation. The supernatant was analyzed by HPLC to determine an amount of a product.

EXAMPLE 1

Formation of a Recombinant Vector

A method for obtaining a plant phenylalanine ammonia lyase gene used in this Example is described in detail in a prior application (JP-A-2003-225092) of the present inventors. Although the recombinant vector described in JP-A-2003-225092 could be used, plasmid pQEPAL2/ΔHis6 (refer to FIG. 1) obtained by deleting His-tag coding sequence from recombinant vector pQEPAL2 described in the Yazaki et al. report (Biosci. Biotech. Biochem. (1997), 61 (12), 1995-2003) was prepared, and used here.

Figure 1:
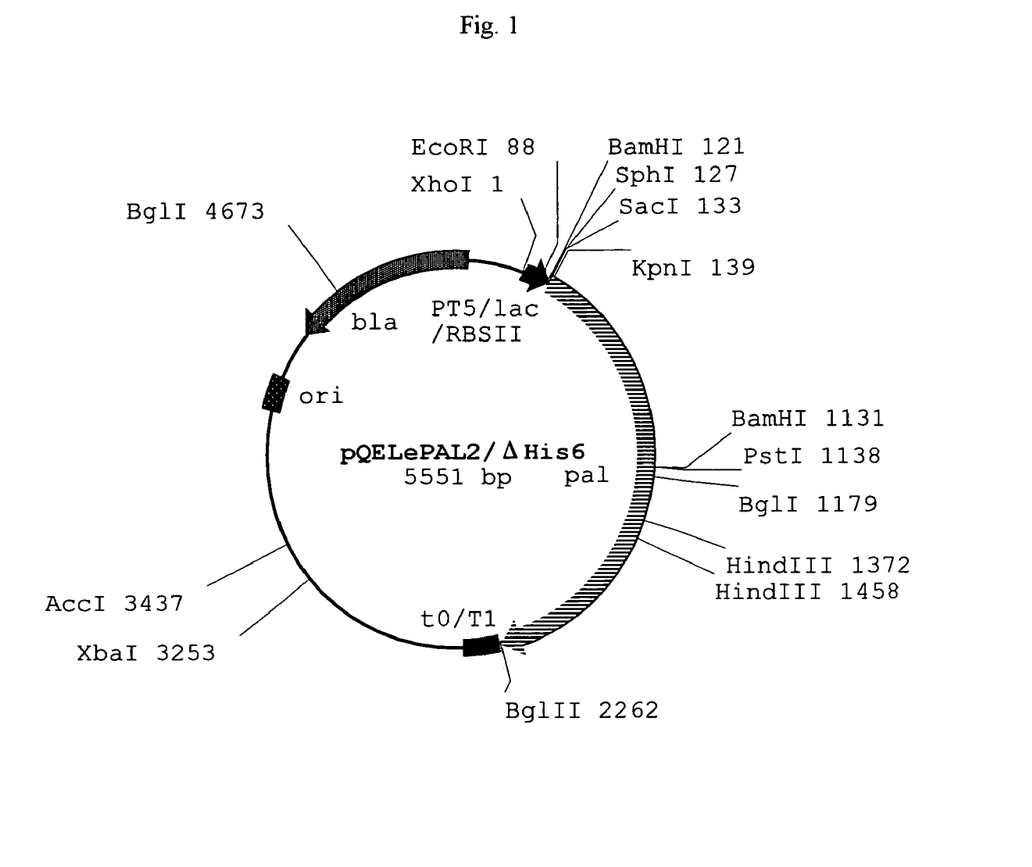
FIG. 1 is a restriction map of a plasmid used in Examples.

In FIG. 1, meanings of symbols are as follows. PT5: T5 promoter; lac: lac operator; RBSII: synthetic ribosome binding site; pal: phenylalanine ammonia lyase gene; t0/T1: transcription terminator; 6xHis: His-tag coding sequence; ORI: origin of replication; bla: β-lactamase gene=ampicillin resistance gene.

For deleting His-tag coding sequence from pQEPAL 2, a primer described in SEQ ID No. 1 (5' side; 18-mer oligonucleotide) and a primer described in SEQ ID No. 2 (3' side; 18-mer oligonucleotide) corresponding to positions before and after His-tag coding sequence of a recombinant vector were synthesized, the portions except His-tag coding sequence were amplified by PCR under the following conditions, and after blunt-ending and phosphorylation, self-ligation was conducted. The following primer of SEQ ID No. 1 was subjected to single base substitution in order for one Hind III site derived from the vector to disappear by which a desired product could easily be recognized.

[PCR Conditions]

Composition of a Reaction Solution:

| template plasmid | 1 µg |
| primer | 100 pmol each |
| dNTP solution | 1 mM each |
| 10 × reaction buffer | 10 µl |
| ExTaqDNA polymerase (manufactured by Takara Shuzo Co., Ltd.) | 2.5 U |
| | 50 µl in total |

Reaction Conditions:

| thermal denaturation | 94° C., 30 seconds |
| annealing | 55° C., 60 seconds |
| elongation | 72° C., 300 seconds |
| cycle number | 30 |

When a vector fragment was amplified under the foregoing conditions, a fragment having a fragment length of approximately 5.5 kb as theoretically calculated was almost distinctively amplified. The fragment was subjected to self ligation according to a standard protocol of TaKaRa BKL Kit (manufactured by Takara Shuzo Co., Ltd.) using this PCR reaction solution. Subsequently, host *Escherichia coli* JM109 strain was transformed with the ligation solution, and the transformant was plated on LB agar plate medium containing 100 ppm ampicillin, and cultured at 35° C. for 24 hours.

Plasmids were prepared from the resulting six colonies using QIAprep Miniprep Kit (manufactured by QIAGEN, Inc.), and a cut pattern was examined with restriction enzyme Hind III. As a result, it was confirmed that all of the plasmids extracted from the six colonies were desired plasmids with His-tag coding sequence removed therefrom.

EXAMPLE 2

Formation of a Transformant Showing PAL (phenylalanine ammonia lyase) Activity

*Escherichia coli* XL1-Blue strain transformed with pQE-PAL2/ΔHis6 obtained in Example 1 was plated on LB agar plate medium containing 0.1 mM isopropyl-β-D-thiogalactopyranoside (IPTG) and 100 ppm ampicillin, and cultured at 25° C. for 48 hours to form colonies of various sizes. From these colonies, 24 strains were arbitrarily selected, and cultured in 5 ml of LB medium. After 34 hours from the start-up of culture, isopropyl-β-D-thiogalactopyranoside (IPTG) was added to the culture solution in an amount of 0.1 mM, and the mixture was further cultured for 4 hours. The resulting culture solution was centrifuged to collect cells, and the resulting cells were subjected to a reaction by the foregoing method. After the reaction for 3 hours, the amount of the product was determined by HPLC. Consequently, as shown in Table 2, the transformants showed various relative activities in the range of from 0 to 4 on condition that the activity of the unreacted transformant was defined as 1.

TABLE 2

| Colony No. | Relative activity |
|---|---|
| unseparated | 1.0 |
| 1 | 1.3 |
| 2 | 1.0 |
| 3 | 0.6 |
| 4 | 0.2 |
| 5 | 0.2 |
| 6 | 0.2 |
| 7 | 3.0 |
| 8 | 3.7 |
| 9 | 0 |
| 10 | 2.8 |
| 11 | 0.3 |
| 12 | 0 |
| 13 | 1.0 |
| 14 | 1.4 |
| 15 | 1.3 |
| 16 | 0 |
| 17 | 0.9 |
| 18 | 1.5 |
| 19 | 1.9 |
| 20 | 0.9 |
| 21 | 1.0 |
| 22 | 0.3 |
| 23 | 3.7 |
| 24 | 0.3 |

EXAMPLE 3

Activity of a Transformant After Separation and Subculture of Single Colonies

All of the 24 colony strains obtained in Example 2 were streaked on LB agar plate medium containing 0.1 mM isopropyl-β-D-thiogalactopyranoside (IPTG) and 100 ppm ampicillin, and cultured at 25° C. for 48 hours. In the same manner as in Example 2, the separated colonies were cultured, and the activities thereof were measured. Consequently, strains with activities changed appeared as shown in Table 3.

TABLE 3

| Colony No. | Relative activity | Behavior |
|---|---|---|
| unseparated | 1.0 | |
| 1 | 1.2 | → |
| 2 | 0.9 | ↓ |
| 3 | 0.6 | → |
| 4 | 0 | → |
| 5 | 0.2 | → |
| 6 | 0.2 | → |
| 7 | 5.6 | ↑ |
| 8 | 5.8 | ↑ |
| 9 | 0 | → |
| 10 | 5.5 | ↑ |

TABLE 3-continued

| Colony No. | Relative activity | Behavior |
|---|---|---|
| 11 | 0.1 | ↓ |
| 12 | 0 | ↓ |
| 13 | 0.9 | ↓ |
| 14 | 1.2 | ↓ |
| 15 | 1.0 | ↓ |
| 16 | 0 | ↓ |
| 17 | 0.7 | ↓ |
| 18 | 1.5 | → |
| 19 | 2.6 | ↑ |
| 20 | 0.8 | ↓ |
| 21 | 0.9 | → |
| 22 | 0.3 | → |
| 23 | 5.8 | ↑ |
| 24 | 0.3 | → |

The strains showing high activities in the activity measurement were compared with the other strains. No. 7 colony was poor in growth. However, No. 8 strain, No. 10 strain and No. 23 strain all showed a color tone of significantly whitish with surface gloss, and were different in shape.

EXAMPLE 4

Method for Identifying a High-activity Strain by Stress Response

For examining whether or not there are characteristics easily and surely identifiable without relying on a visual identifying observation method which involves a lot of noise, hydrogen peroxide decomposition activity and growth recovery after heat treatment (heat resistance) were measured for each strain. Regarding the hydrogen peroxide decomposition activity, several microliters of a hydrogen peroxide aqueous solution were added to the streak-cultured cells on the LB agar plate medium, and a condition of bubble occurrence on the plate was observed.

In a test for heat resistance, the cells on the agar plate were cultured on the M9 medium for 16 hours, then collected by centrifugation, suspended in a physiological saline solution, and gently shaken for 8 hours to form stationary cells. The stationary cells were treated at 55° C. for 2 hours, then streaked on LB agar plate medium containing 100 ppm ampicillin, and cultured at 25° C.

As a result of this test, such a tendency was observed that the high-activity strains were high in hydrogen peroxide decomposition activity from the initial growth phase in comparison to general and low-activity strains. Meanwhile, such a tendency was observed that the two of the three strains were high in heat resistance, but one strain was, like ordinary strains, poor in growth. Accordingly, the separative selection of high-activity strains was attempted using the shape of the colony and the hydrogen peroxide decomposition activity at the initial growth phase as indexes.

EXAMPLE 5

Separative Selection of High-activity Transformants

In the same manner as in Example 1, Escherichia coli XL1-Blue strain transformed with pQEPAL2/ΔHis6 was plated on LB agar plate medium containing 0.1 mM isopropyl-β-D-thiogalactopyranoside (IPTG) and 100 ppm ampicillin, and cultured at 25° C. for 48 hours. 1 μl of a 30% hydrogen peroxide aqueous solution was added such that the solution was brought into contact with a part of each colony formed, and bubbling by decomposition was observed. Consequently, vigorous bubbling was observed in some colonies. Of these, 24 colony strains were isolated, inoculated in M9 agar plate medium containing 100 ppm ampicillin, and cultured at 25° C. for 48 hours.

In the same manner as in Example 2, the isolated 24 strains were cultured, and the activities thereof were measured. As a result, the high activities were observed in all of the strains as shown in Table 4. Of these, three strains were selected which were relatively good in growth condition and clear in colony formation.

TABLE 4

| Colony No. | Relative activity |
| --- | --- |
| unseparated | 1.0 |
| 1 | 5.9 |
| 2 | 5.6 |
| 3 | 5.7 |
| 4 | 6.1 |
| 5 | 6.2 |
| 6 | 5.5 |
| 7 | 5.6 |
| 8 | 6.0 |
| 9 | 6.1 |
| 10 | 5.4 |
| 11 | 5.8 |
| 12 | 5.2 |
| 13 | 6.2 |
| 14 | 6.1 |
| 15 | 5.3 |
| 16 | 6.3 |
| 17 | 5.9 |
| 18 | 5.6 |
| 19 | 6.2 |
| 20 | 6.3 |
| 21 | 6.3 |
| 22 | 5.7 |
| 23 | 5.9 |
| 24 | 5.4 |

EXAMPLE 6

Subculture Stability of High-activity Strains

Each of high-activity strains Nos. 16, 20 and 21 selected was streaked on LB agar plate medium containing 100 ppm ampicillin, and cultured at 25° C. for 48 hours. The cultured cells were streak-cultured in the same LB agar plate medium five times. During each subculture, the cells were cultured as in Example 2, and change in activity was observed in each subculture. As shown in Table 5, the two (Nos. 16 and 20) of these strains were low in change in activity due to the subculture, and were confirmed to show high activities as a stable character.

TABLE 5

| Colony No. | Relative activity | | | | | |
| --- | --- | --- | --- | --- | --- | --- |
| Number of subcultures | at the start-up | 1 | 2 | 3 | 4 | 5 |
| unseparated | 1.0 | 0.5 | | | | |
| 16 | 6.3 | 5.8 | 6.0 | 6.1 | 6.0 | 5.9 |
| 20 | 6.3 | 6.3 | 5.9 | 6.2 | 6.1 | 6.3 |
| 21 | 6.3 | 5.9 | 5.8 | 5.5 | 5.0 | 5.2 |

EXAMPLE 7

Confirmation of a Plasmid of a High-activity Strain

For examining which of plasmid mutation and host mutation is responsible for the change in activity, No. 16 strain was selected from the two strains found to show stable high activity, and its holding plasmid was prepared. The entire base sequence (approximately 5.5 kb) thereof and the activity of the re-transformant were examined.

The plasmid was extracted using QIAprep Spin Miniprep Kit (manufactured by QIAGEN Inc.), and the entire base sequence was decoded by gene walking analysis of both chains. The sequence was determined by a standard use method of DNA sequencer model 377 ver. 3.0, namely a standard PCR reaction and electrophoresis data analytical method. Binding of partial sequences determined was conducted with a nucleic acid sequence automatic binding software GENETYX-WIN/ATSQ (manufactured by Software Development Co., Ltd.). As a result, it was confirmed that abnormality such as substitution or loss was not observed in the entire sequence.

*Escherichia coli* XL1-Blue strain was transformed with the foregoing plasmid. The transformant was plated on LB agar plate medium containing 0.1 mM isopropyl-β-D-thiogalactopyranoside (IPTG) and 100 ppm ampicillin, and cultured at 25° C. for 48 hours. Consequently, colonies having various sizes were formed as described in Example 2. From the colonies, 24 strains were arbitrarily selected, and cultured and measured for activity as in Example 2. As a result, the transformants showed various relative activities in the range of from 0 to 3 on condition that the activity of the unseparated transformant was defined as 1.

From these facts, it was confirmed that the plasmid extracted from the high-activity strain was exactly the same as the plasmid before selective separation and the high activity was not attributed to the change of the plasmid but to the change of the host *Escherichia coli*.

TABLE 6

| Colony No. | Relative activity |
| --- | --- |
| unseparated | 1.0 |
| 1 | 0 |
| 2 | 1.2 |
| 3 | 0.2 |
| 4 | 0.4 |
| 5 | 1.7 |
| 6 | 2.7 |
| 7 | 3.2 |
| 8 | 0 |
| 9 | 2.2 |
| 10 | 2.8 |
| 11 | 0.1 |
| 12 | 1.0 |
| 13 | 0.8 |
| 14 | 1.9 |
| 15 | 2.9 |
| 16 | 0 |
| 17 | 0.5 |
| 18 | 0.2 |
| 19 | 0 |
| 20 | 0.1 |
| 21 | 1.7 |
| 22 | 3.1 |
| 23 | 1.1 |
| 24 | 0 |

EXAMPLE 8

Confirmation of Protein Production by a High-activity Strain

High-activity strain No. 16 obtained in Example 6 and colony Nos. 24 and 12 of Example 7 were cultured on 5 ml of LB medium containing 100 ppm ampicillin according to the method described in Example 2. After 34 hours of the culture, 0.1 mM isopropyl-β-D-thiogalactopyranoside (IPTG) was added, and the mixture was further cultured for 4 hours. Turbidity (660 nm) of the resulting culture solution was measured, and it was confirmed to be approximately the same turbidity. Then, 0.1 ml of the culture solution was centrifuged to collect cells. The cells were suspended in 0.15 ml of a physiological saline solution, and 0.05 ml of a 4×SDS electrophoresis sample treating solution (obtained by mixing 2.1 ml of 1 M Tris-HCl (pH 6.8), 860 mg of SDS, 2 ml of 2-mercaptoethanol, 2.8 ml of glycerol and 1 mg of BPB and adjusting the mixture to 10 ml with deionized water) was added thereto and mixed well therewith. The mixture was then boiled at 100° C. for 5 minutes.

The treated solution was centrifuged (12,000 rpm×5 minutes) to remove a precipitate, and 10 μl of the resulting supernatant was subjected to 10 to 20% polyacrylamide gel electrophoresis (twice).

Figure 2:
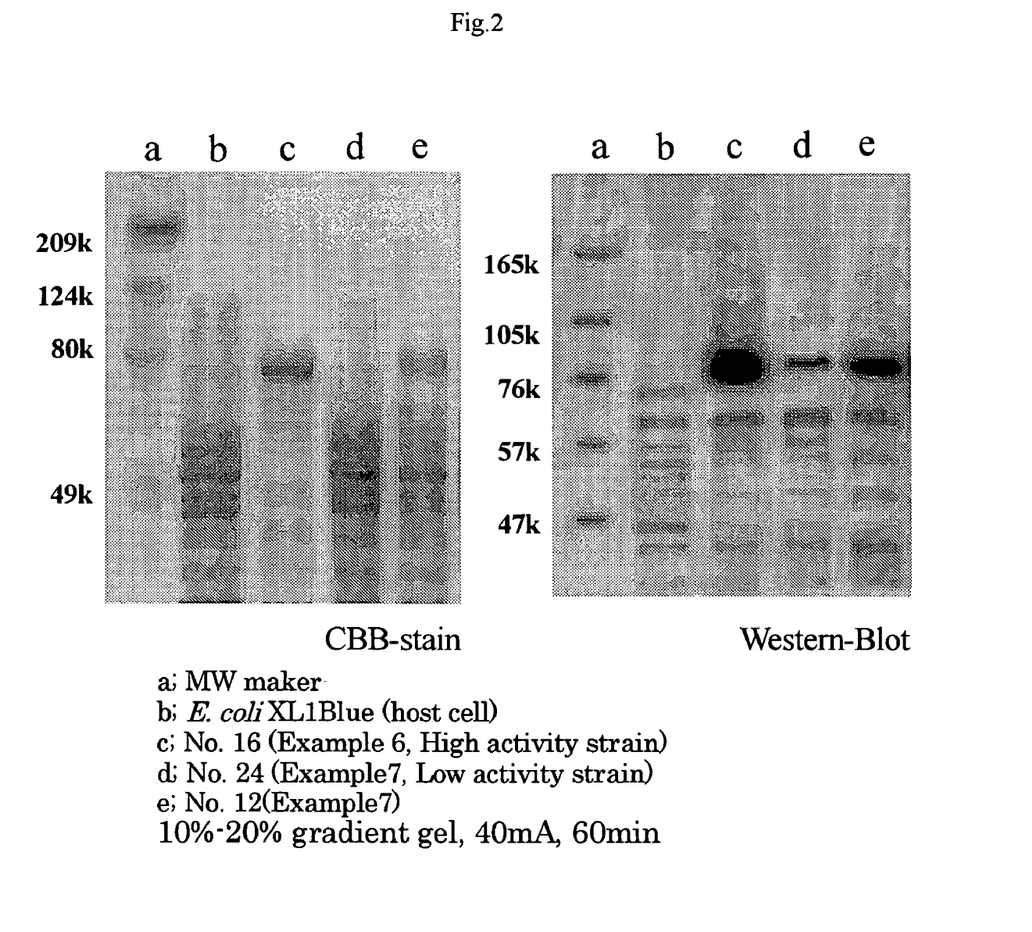
FIG. 2 is the results of SDS-PAGE and western blotting.

One of the acrylamide gels after separation was subjected to protein dyeing with a CBB dyeing solution. With respect to the other gel, a protein was transferred to a nitrocellulose film by electroblotting under standard conditions, and western blotting was conducted according to a standard method of Phototope-HRP Western Blot Detection System (manufactured by Amersham PLC) using an anti-PAL (rabbit) antibody as a primary antibody. Consequently, the activity was confirmed to agree with the amount of the PAL (phenylalanine ammonia lyase) protein formed (refer to FIG. 2.).

EXAMPLE 9

Removal of a Plasmid from a High-activity Strain

High-activity strain No. 16 obtained in Example 6 was cultured on 5 ml of LB medium containing 20 ppm tetracycline at 35° C. for 24 hours, and a part of the culture solution was inoculated and subcultured under the same conditions. This procedure was repeated for 10 days. The culture solution on day 10 was plated on LB agar plate medium, and cultured at 35° C. for 24 hours to form colonies.

From the resulting colonies, 50 colonies were arbitrarily selected, inoculated in LB agar plate medium containing 20 ppm tetracycline and 100 ppm ampicillin and in LB agar plate medium containing only 20 ppm tetracycline, and cultured at 25° C. for 48 hours. The strain which was not grown in the ampicillin-containing medium but was grown in the ampicillin-free medium was isolated, and designated *Escherichia coli* SD840.

EXAMPLE 10

Reaction Using a High-activity Strain

High-activity strain No. 16 obtained in Example 6 was cultured on 100 ml of LB medium containing 100 ppm ampicillin according to the method described in Example 2. This culture solution was further inoculated in 5 L jar fermenter containing 100 ppm ampicillin and 0.1 mM isopropyl-β-D-thiogalactopyranoside (IPTG), and subjected to aerated agitation culture at 30° C. and 800 rpm for 38 hours by aeration at 1 ml/min.

Cells obtained by centrifugation of the culture solution at the stationary phase were resuspended in 1 L of 4 M ammonia/ammonium carbonate (pH 10.3), and 20 g of cinnamic acid was added thereto. The reaction was conducted with stirring at 30° C. and 800 rpm. A part of the reaction solution was sampled every 1 hour, and an amount of L-phenylalanine formed in the reaction solution was determined by HPLC. While a substrate was successively added to keep a substrate concentration at 2%, the reaction was continued. Then, approximately 3.5% L-phenylalanine was accumulated in the reaction solution for approximately 3 hours.

INDUSTRIAL APPLICABILITY

According to the selection method of the invention, *Escherichia coli* which expresses an exogenous gene stably at a high level, especially *Escherichia coli* which expresses a gene hard to express in *Escherichia coli* stably at a high level can be selected easily and surely. A plant-derived ammonia lyase has been considered as a gene hard to express in *Escherichia coli*. However, according to the method of the invention, a plant-derived ammonia lyase gene can highly be expressed stably. It is therefore useful for synthesizing compounds such as L-amino acids and anthocyanin by addition of an amino group to various unsaturated carboxylic acids.

The invention claimed is:
1. *Escherichia coli* SD840 strain (Deposit No. FERM BP-08546).

* * * * *